US009453223B2

(12) United States Patent
Jagadeeswaran

(10) Patent No.: US 9,453,223 B2
(45) Date of Patent: *Sep. 27, 2016

(54) PIGGY BACK DELIVERY OF NUCLEIC ACIDS INTO ORGANISMS

(71) Applicant: University of North Texas, Denton, TX (US)

(72) Inventor: Pudur Jagadeeswaran, Denton, TX (US)

(73) Assignee: University of North Texas, Denton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,423

(22) Filed: May 18, 2015

(65) Prior Publication Data

US 2015/0247146 A1 Sep. 3, 2015

Related U.S. Application Data

(62) Division of application No. 13/782,645, filed on Mar. 1, 2013, now Pat. No. 9,062,090.

(60) Provisional application No. 61/605,851, filed on Mar. 2, 2012.

(51) Int. Cl.

| *A61K 31/70* | (2006.01) |
|---|---|
| *C07H 21/02* | (2006.01) |
| *C07H 21/04* | (2006.01) |
| *C12N 15/113* | (2010.01) |
| *A61K 31/7105* | (2006.01) |
| *A61K 31/711* | (2006.01) |
| *A61K 31/713* | (2006.01) |
| *C12N 15/11* | (2006.01) |
| *C12Q 1/68* | (2006.01) |
| *G01N 33/50* | (2006.01) |
| *C12N 5/00* | (2006.01) |
| *A61K 48/00* | (2006.01) |

(52) U.S. Cl.
CPC ........... *C12N 15/113* (2013.01); *A61K 31/711* (2013.01); *A61K 31/713* (2013.01); *A61K 31/7105* (2013.01); *A61K 48/005* (2013.01); *C07H 21/02* (2013.01); *C12N 15/111* (2013.01); *C12Q 1/6883* (2013.01); *G01N 33/5023* (2013.01); *A61K 48/00* (2013.01); *C12N 2310/11* (2013.01); *C12N 2310/18* (2013.01); *C12N 2310/313* (2013.01); *C12N 2310/315* (2013.01); *C12N 2310/3181* (2013.01); *C12N 2310/3233* (2013.01); *C12N 2310/336* (2013.01); *C12N 2310/53* (2013.01); *C12N 2320/32* (2013.01); *C12Q 2600/136* (2013.01); *C12Q 2600/178* (2013.01)

(58) Field of Classification Search
None
See application file for complete search history.

(56) References Cited

U.S. PATENT DOCUMENTS

| 7,935,816 B2 | 5/2011 | Li |
| 2009/0171075 A1 | 7/2009 | Li |
| 2010/0292306 A1 | 11/2010 | Carlson et al. |
| 2011/0190287 A1 | 8/2011 | Jagadeeswaran |

OTHER PUBLICATIONS

C.S. Cobbs, T.R. Whisenhunt, D.R. Wesemann, L.E. Harkins, E.G. Van Meir, and M. Samanta, Inactivation of wild-type p53 protein function by reactive oxygen and nitrogen species in malignant glioma cells. Cancer Res 63 (2003) 8670-3.
M. Gregory, R. Hanumanthaiah, and P. Jagadeeswaran, Genetic analysis of hemostasis and thrombosis using vascular occlusion. Blood Cells Mol Dis 29 (2002) 286-95.
R.M. Hudziak, J. Summerton, D.D. Weller, and P.L. Iversen, Antiproliferative effects of steric blocking phosphorodiamidate morpholino antisense agents directed against c-myc. Antisense Nucleic Acid Drug Dev 10 (2000) 163-76.
P.A. Morcos, Y. Li, and S. Jiang, Vivo-Morpholinos: a non-peptide transporter delivers Morpholinos into a wide array of mouse tissues. Biotechniques 45 (2008) 613-4, 616, 618 passim.
J.D. Moulton, and S. Jiang, Gene knockdowns in adult animals: PPMOs and vivo-morpholinos. Molecules 14 (2009) 1304-23.
A. Nasevicius, and S.C. Ekker, Effective targeted gene 'knockdown' in zebrafish. Nat Genet 26 (2000) 216-20.
Nazmi, A., et al., "Antiviral and Neuroprotective Role of Octaguanidinium Dendrimer-Conjugated Morpholino Oligomers in Japanese Encephalitis," PLoS Negl Trop Dis (2010) 4:11 1-12.
I.A. Shestopalov, S. Sinha, and J.K. Chen, Light-controlled gene silencing in zebrafish embryos. Nat Chem Biol 3 (2007) 650-1.
Wu, B., et al., "Targeted Skipping of Human Dystrophin Exons in Transgenic Mouse Model Systemically for Antisense Drug Development," PLoS Negl Trop Dis (2011) 6:5 1-11.

*Primary Examiner* — Sean McGarry
(74) *Attorney, Agent, or Firm* — Edwin S. Flores; Chainey P. Singleton; Chalker Flores, LLP

(57) ABSTRACT

The present invention includes nucleic acid hybrid molecules capable of entering cells comprising at least one vivo-morpholino oligonucleotide (vivo-MO) comprising a guanidine-rich head conjugated to the 5' end, and at least one standard oligonucleotide comprising a gene-specific sequence and a standard oligonucleotide pairing sequence, wherein the standard oligonucleotide is bound to the vivo-morpholino oligonucleotide through base pairing to form a hybrid and wherein the vivo-morpholino oligonucleotide pairing sequence is complementary to the standard oligonucleotide pairing sequence.

24 Claims, 4 Drawing Sheets

Figure 4a:
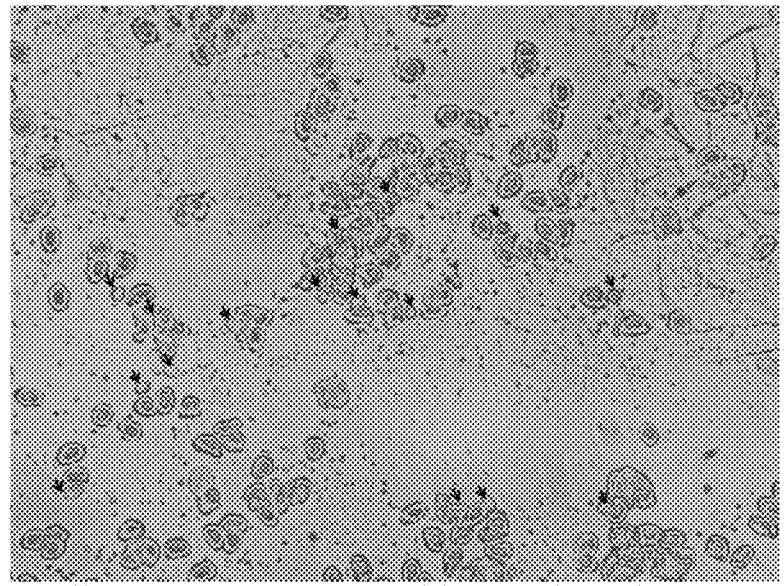
Figure 4b:
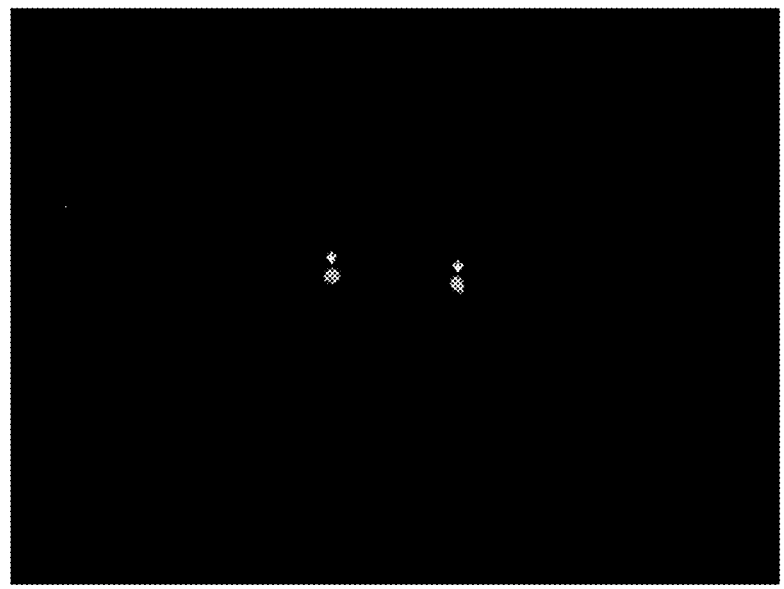
*Figure 4*

PIGGY BACK DELIVERY OF NUCLEIC ACIDS INTO ORGANISMS

CROSS-REFERENCE TO RELATED APPLICATIONS

This patent application is a divisional application of U.S. patent application Ser. No. 13/782,645 filed on Mar. 1, 2013 and entitled "Piggy Back Delivery of Nucleic Acids Into Organisms," which claims priority to U.S. Provisional Patent Application Ser. No. 61/605,851, filed Mar. 2, 2012.

TECHNICAL FIELD OF THE INVENTION

Provided are, in general, nucleic acid hybrid molecules capable of entering cells comprising at least one vivo-morpholino oligonucleotide (vivo-MO) and a standard oligonucleotide comprising a gene-specific sequence; methods of introducing standard oligonucleotides into cells; nucleic acid hybrid molecules for treating patients; and methods of performing a clinical trials.

STATEMENT OF FEDERALLY FUNDED RESEARCH

None.

INCORPORATION-BY-REFERENCE OF MATERIALS FILED ON COMPACT DISC

The present application includes a Sequence Listing filed separately as required by 37 CFR 1.821-1.825.

BACKGROUND OF THE INVENTION

Without limiting the scope of the invention, its background is described in connection with piggy-back delivery of nucleic acids into organisms.

U.S. Pat. No. 7,935,816 issued to Yong-Fu Li (2011) describes preparations of molecular transporter compositions and their use for transporting bioactive substances into cells in living animals. For in vivo delivery, the composition is covalently linked to the bioactive substance and the resultant composite structure is introduced into the subject. The transporter composition includes multiple guanidine moieties on a dendrimeric scaffold having a triazine core.

U.S. Patent Application Publication No. 20110190287 to Pudur Jagadeeswaran (2011) describes compounds comprising a guanidine-rich head covalently coupled to one or more oligonucleotide antisense sequences which are useful to modulate blood coagulation by affecting the expression of integrin α.IIb or β.3. Included are also pharmaceutical compositions containing these compounds, with or without other therapeutic agents, and well as methods of using these compounds as inhibitor of platelet aggregation, as thrombolytics, and/or for the treatment of other thromboembolic disorders. Vivo-MOs, which include eight guanidine groups dendrimerically arranged in the guanidine-rich head and two synthetic antisense morpholino oligonucleotides, are representative compounds.

U.S. Patent Application Publication No. 20100292306 to George Carlson et al (2010) describes compositions and methods for treatment of individuals diagnosed with a dystrophin deficiency are disclosed. In particular, inhibitors of NF.K.B transactivation and/or inhibitors that suppress p65 expression are used to prevent and/or reverse muscle damage in animals or humans lacking dystrophin. Such compositions and methods are useful in the treatment of individuals with muscular dystrophy. In an embodiment of the present disclosure a subject diagnosed with Duchenne muscular dystrophy may be treated with an agent that is a specific translation blocking vivo-morpholino to decrease the level or the activity of the p65 subunit of NF.K.B in the muscular tissues of the subject.

Wu et al., Targeted skipping of human dystrophin exons in transgenic mouse model systemically for antisense drug development, PLoS One. 2011; 6(5):e19906. Epub 2011 May 17, describes application of vivo-morpholino to an hDMD mouse, a transgenic model carrying the full-length human dystrophin gene, and more than 70% efficiency of targeted human dystrophin exon skipping in vivo systemically. We also established a GFP-reporter myoblast culture to screen AOs targeting human dystrophin exon 50. Antisense efficiency for most AOs was consistent between the reporter cells, human myoblasts and in the hDMD mice in vivo. But variation in efficiency was also clearly observed.

Nazmi et al, Antiviral and neuroprotective role of octaguanidinium dendrimer-conjugated morpholino oligomers in Japanese encephalitis, PLoS Negl Trop Dis. 2010 Nov. 23; 4(11):e892.

SUMMARY OF THE INVENTION

The present invention includes nucleic acid hybrid molecule capable of entering cells comprising at least one vivo-morpholino oligonucleotide (vivo-MO) comprising a guanidine-rich head conjugated to the 5' end, and at least one standard oligonucleotide comprising a gene-specific sequence and a standard oligonucleotide pairing sequence, wherein the standard oligonucleotide is bound to the vivo-morpholino oligonucleotide through base pairing to form a hybrid, and wherein the vivo-morpholino oligonucleotide pairing sequence is complementary to the standard oligonucleotide pairing sequence. In certain aspects of the invention, the gene-specific sequence comprises a sequence that is antisense to an mRNA or a pre-mRNA and/or is complementary to at least one coding DNA, noncoding DNA, or a splice site; the standard oligonucleotide may comprise a DNA oligonucleotide, a RNA, a siRNA or a RNAi, and/or a gene. In certain aspects of the invention, the standard oligonucleotide may be selected from the group consisting of phosphorodithio oligonucleotide, phosphorothio oligonucleotide, locked oligonucleotide, and peptide nucleic acid. The standard oligonucleotide pairing sequence may be located 3' of the gene-specific sequence, whereby the standard oligonucleotide has a 5' overhanging end of 20-30 nucleotides. In certain aspects, the morpholino oligonucleotide pairing sequence and the gene-specific oligonucleotide pairing sequence may be 12-20 long; the guanidine-rich head may comprise a dendrimeric octaguinidine. Embodiments of the invention includes methods of introducing a standard oligonucleotide into a cell comprising obtaining a standard oligonucleotide comprising a gene-specific sequence and a standard oligonucleotide pairing sequence, obtaining a vivo-morpholino oligonucleotide (vivo-MO) comprising a guanidine-rich head conjugated to the 5' end and a vivo-morpholino oligonucleotide pairing sequence that is complementary to the standard oligonucleotide pairing sequence, binding the standard oligonucleotide to the vivo-morpholino oligonucleotide, wherein a nucleic acid hybrid molecule is formed, and contacting a cell with the nucleic acid hybrid molecule. The cell may have been previously isolated and contacting the cell with the nucleic acid hybrid molecule may be selected from the group consisting of administering the nucleic acid hybrid molecule to a vertebrate orally, intravenously, intramuscularly, intraperitoneally, subcutaneously, by intranasal instillation, by application to mucous membranes, and by instillation into hollow organ walls or newly vascularized blood vessels. Contacting the cell with the nucleic acid hybrid molecule may also comprise treating a patient afflicted with a disease selected from the group consisting of diabetes, cancer, thalassemia, sickle cell disease, hemophilia, viral hepatitis, AIDS, genetic disease, and infectious disease. In certain aspects, the method may further comprise determining a gene expression of a gene complementary to the gene-specific sequence, and the standard oligonucleotide may be selected from the group consisting of a DNA oligonucleotide, a RNA, a RNAi, a siRNA, phosphorodithio oligonucleotide, a phosphorothio oligonucleotide, a locked oligonucleotide, and a peptide nucleic acid. The standard oligonucleotide may comprise a gene, and the guanidine-rich head may comprise a dendrimeric octaguinidine. The present invention also includes methods to treat a patient suspected of having a disease comprising obtaining a nucleic acid hybrid molecule capable of entering cells comprising at least one standard oligonucleotide comprising a gene-specific sequence and a standard oligonucleotide pairing sequence, at least one vivo-morpholino oligonucleotide (vivo-MO) comprising a guanidine-rich head conjugated to the 5' end, wherein the vivo-morpholino oligonucleotide pairing sequence is complementary to the standard oligonucleotide pairing sequence, and wherein the standard oligonucleotide is bound to the vivo-morpholino oligonucleotide through base pairing, forming a hybrid; and contacting the patient with the nucleic acid hybrid molecule. The methods may also comprise obtaining a sample from the patient and determining gene expression of a gene that is homologous, antisense, or complementary to the gene-specific sequence. The disease may be selected from the group consisting of diseases treatable by reducing a translation of a gene, wherein the gene is a c-myc gene and the disease is Burkitt's lymphoma or the gene is a ras oncogene and the disease is adenocarcinomas, a thyroid tumor, or a pancreatic tumor, and contacting the patient with the nucleic acid hybrid molecule may be selected from the group consisting of administering the nucleic acid hybrid molecule orally, intravenously, intramuscularly, intraperitoneally, subcutaneously, by intranasal instillation, by application to mucous membranes, and by instillation into hollow organ walls or newly vascularized blood vessels. In certain aspects, the standard oligonucleotide is selected from the group consisting of a DNA oligonucleotide, a RNA, a RNAi, a siRNA, a phosphorodithio oligonucleotide, a phosphorothio oligonucleotide, a locked oligonucleotide, and a peptide nucleic acid, and the nucleic acid hybrid molecule may comprise a standard oligonucleotide comprising a gene-specific sequence and a standard oligonucleotide pairing sequence, a vivo-morpholino oligonucleotide (vivo-MO) comprising a guanidine-rich head conjugated to the 5' end and a vivo-morpholino oligonucleotide pairing sequence that is complementary to the standard oligonucleotide pairing sequence, the standard oligonucleotide bound to the vivo-morpholino oligonucleotide through base pairing, forming a hybrid nucleic acid. In certain aspects, the disease may be selected from the group consisting of diabetes, cancer, genetic disorder, diabetes, infectious disease, hemophilia, thalassemia, sickle cell disease, and Duchene Muscular dystrophy etc. In certain embodiments, the invention includes methods of performing a clinical trial to evaluate a candidate drug believed to be useful in treating a disease by affecting the expression of a gene complementary, antisense, or homologous to a gene-specific sequence, the method comprising: (a) obtaining the candidate drug comprising a nucleic acid hybrid molecule capable of entering cells comprising at least one standard oligonucleotide comprising the gene-specific sequence and a standard oligonucleotide pairing sequence, at least one vivo-morpholino oligonucleotide (vivo-MO) comprising a guanidine-rich head conjugated to the 5' end; wherein the vivo-morpholino oligonucleotide pairing sequence is complementary to the standard oligonucleotide pairing sequence; and wherein the standard oligonucleotide is bound to the vivo-morpholino oligonucleotide through base pairing, forming a hybrid (b) administering the candidate drug to a first subset of patients, and a placebo to a second subset of patients; a comparable drug to a second subset of patients; or a drug combination of the candidate drug and another active agent to a second subset of patients; (c) monitoring the progression of the disease in the first subset of patients as compared to the second subset of patients, wherein a relative and statistically significant improvement of the disease in the first subset of patients indicates that the candidate drug is useful in treating the disease. In certain embodiments, the invention includes methods to identify a nucleic acid hybrid molecule effective in reducing an expression of a gene comprising: obtaining a first and at least a second nucleic acid hybrid molecule, each nucleic acid hybrid molecule comprising at least one standard oligonucleotide comprising a sequence specific for the gene and a standard oligonucleotide pairing sequence; each nucleic acid hybrid molecule further comprising at least one vivo-morpholino oligonucleotide (vivo-MO) comprising a guanidine-rich head conjugated to the 5' end, wherein the vivo-morpholino oligonucleotide pairing sequence is complementary to the standard oligonucleotide pairing sequence, and wherein the standard oligonucleotide is bound to the vivo-morpholino oligonucleotide through base pairing, forming a hybrid, contacting the first and at least the second nucleic acid hybrid molecules with at least one cell each; and determining the expression of the gene in the cells contacted with the first and at least the second nucleic acid hybrid molecules; identifying the nucleic acid hybrid molecules effective in reducing the expression of the gene. In certain aspects, the methods further comprise determining the expression of a control gene and identifying the nucleic acid hybrid molecule that does not affect the expression of the control gene. In certain embodiments, the invention includes methods to reduce an expression of a gene comprising obtaining a standard oligonucleotide comprising a gene-specific sequence and a standard oligonucleotide pairing sequence, obtaining a vivo-morpholino oligonucleotide (vivo-MO) comprising a guanidine-rich head conjugated to the 5' end and a vivo-morpholino oligonucleotide pairing sequence that is complementary to the standard oligonucleotide pairing sequence, binding the standard oligonucleotide to the vivo-morpholino oligonucleotide, wherein a nucleic acid hybrid molecule is formed, and contacting at least one cell with the nucleic acid hybrid molecule, whereby the hybrid molecule enters the cell and whereby the nucleic acid hybrid molecule reduces the expression of the gene. Contacting the cell with the nucleic acid hybrid molecule may be selected from the group consisting of administering the nucleic acid hybrid molecule orally, intravenously, intramuscularly, intraperitoneally, subcutaneously, by intranasal instillation, by application to mucous membranes, and by instillation into hollow organ walls or newly vascularized blood vessels. In addition, contacting the cell with the nucleic acid hybrid molecule may comprise treating a patient afflicted with a disease selected from the group consisting of diabetes, cancer, genetic disease, and infectious disease. In certain aspects, the standard oligonucleotide may be selected from the group consisting of a DNA oligonucleotide, a RNA, a RNAi a siRNA, a phosphorodithio oligonucleotide, a phosphorothio oligonucleotide, a locked oligonucleotide, and a peptide nucleic acid, and/or the guanidine-rich head may comprise a dendrimeric octaguinidine.

BRIEF DESCRIPTION OF THE DRAWINGS

For a more complete understanding of the features and advantages of the present invention, reference is now made to the detailed description of the invention along with the accompanying figures.

FIGS. 4a-4b shows blood smear from TG(fli1:EGFP)y1 transgenic fish treated with EGFP-SO/ngVMO hybrid. Figures a and b are the brightfield and fluorescence images respectively. Note that there are several thrombocytes lacking GFP fluorescence shown by black arrows in 4a. Only a few thrombocytes are GFP positive shown by red arrows in 4a. White arrows in 4b show the GFP thrombocytes.

DETAILED DESCRIPTION OF THE INVENTION

Figure 1:
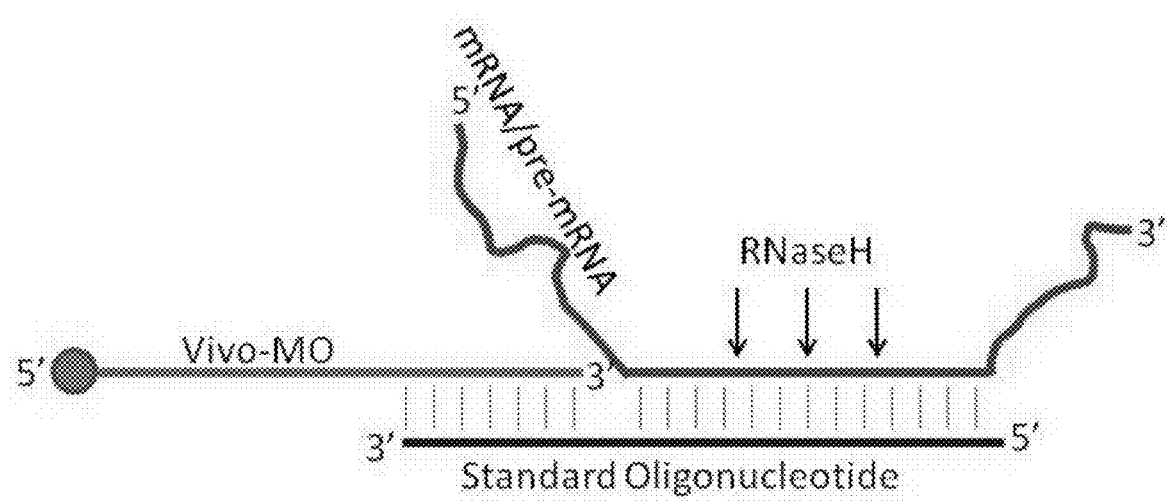
FIG. 1 is a schematic diagram of the hybrid formation. Note the possible hybrid formation (base pairing indicated by small vertical bars) between non-gene Vivo-Morpholino, ngVMO (shown in green) and standard oligonucleotide, SO (shown in blue) as well as hybrid formation between SO and either mRNA or pre-mRNA (shown in red). Arrows show RNaseH cleavage of the mRNA/pre-mRNA portion of the RNA-DNA hybrid. Closed circle represents dendrimeric octaguinidine conjugated at the 5' end of ngVMO.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Knockdown of genes is used to establish the function of genes in animal models as well as in cells. However, application of these methods on a genome wide basis for all the genes (approximately 30,000 genes) has not been accomplished because it is prohibitively expensive; for example performing one knockdown costs approximately $1000. Furthermore, delivering the reagents to cells is also complex and sometimes results in poor efficiencies and toxicities. Knockdowns have been achieved by the use of antisense oligonucleotides and siRNA, e.g., standard oligonucleotides and modified oligonucleotides (MOs and Vivo-MOs as well as phosphorothionates). The inventors recognize that MOs and Vivo-MOs can be used to inhibit gene functions because these MOs are more stable as they are not degraded by nucleases, unlike the standard oligonucleotides. The advantage of Vivo-MOs is that they penetrate the cells and therefore one can deliver them to cells without using special techniques such as microinjection or chemical delivery methods.

The inventors recognized that hybrid molecule can be formed between Vivo-MO and a nucleic acid (standard oligonucleotide) by base pairing, and the hybrid molecule is capable of entering a cell along with the cell penetrating Vivo-MO.

In one example and non-limiting embodiment, the nucleic acid hybrid molecule has the ability to block a gene involved in platelet function, e.g., as a non-limiting model system, zebrafish. In another working model, example, and non-limiting embodiment, the present inventors employed a reagent to target fish whose thrombocytes are labeled with GFP and affirmed loss of GFP signal in thrombocytes. Interestingly to conduct one knockdown by this method is currently only $10. Thus, 20,000 gene knockdowns can be performed easily and in a cost-effective manner. Such principle will lead to the establishment of functions of novel genes in any desired pathway for example in thrombosis, diabetes, heart disease and cancer.

A schematic diagram of an embodiment of a nucleic acid hybrid molecule:

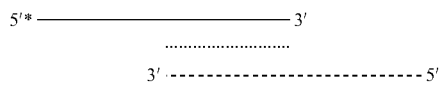

The top strand is the Vivo Morpholino (e.g., 25 nt). * denotes the modification which facilitates the entry of the Vivo-MO. Dots represent base pairing (e.g., 14 bp). The bottom strand standard oligonucleotide. The unpaired region (e.g., 25 nt) of the standard oligonucleotide comprises a gene-specific sequence, e.g., a region that is complimentary to the mRNA of interest, e.g., the target for knockdown.

The knockdown of protein functions by antisense oligonucleotides has been used to understand protein function. The inventors recognize that Vivo-Morpholinos (Vivo-MOs), chemically modified morpholinos that can penetrate cells, can be used in adult experimental animal models to alter pre-mRNA splicing or to block mRNA translation and thereby change the protein expression, e.g., the present inventors have injected thrombocyte-specific αIIb Vivo-MOs intravenously and inhibited thrombocyte function in adult zebrafish. In addition to Vivo-MOs, other antisense oligonucleotides can be used to knockdown protein expression by taking advantage of the endogenous RNaseH mechanism which cleaves target mRNA.

Here, the present inventors introduce nucleic acid hybrid molecules made of a non-gene specific Vivo-MO (ngVMO) and a gene specific standard oligonucleotide (SO). In one embodiment, the hybrid is designed to base pair leaving 5' overhanging ends. The unbasepaired gene specific SO is, at least partially, antisense to the target mRNA/premRNA. The hybrid molecule has the ability to enter cells because the SO is piggy-backed onto the ngVMO. The present inventors have validated this concept by targeting two proteins, αIIb and EGFP, by using the above piggy-backing strategy and found that expression of both proteins was effectively reduced, resulting in both increased bleeding and loss of EGFP. This approach is less expensive and more efficient compared to a Vivo-MO knockdown. Therefore, these nucleic acid hybrid molecules make large-scale functional genomics a realistic goal rather than a multimillion-dollar undertaking. This approach can be used to inhibit undesired protein expression in a variety of human disorders including AIDS. Furthermore, since RNAs and genes can be piggy-backed using ngVMOs, in one embodiment, the present nucleic acid hybrid molecules can be used as gene therapy in cases when protein expression is desirable.

The inventors recognize that antisense oligonucleotides can be used to knockdown protein levels by either translational blocking or splice blocking to control cancer and viral infections with the goal of treating human diseases [1; 2]. This knockdown inhibition can be used in model organisms, such as zebrafish, predominantly through the use of morpholino oligonucleotides (MOs), to study functions of proteins in both development and disease, particularly as a gene discovery tool [3; 4]. These MOs are introduced into the yolks of 1-8-cell-stage zebrafish embryos. Due to the cytoplasmic bridges, MOs rapidly diffuse into these cells allowing ubiquitous cytosolic delivery. However, direct cytosolic delivery of MOs into cells has been difficult to achieve with the exception of microinjections. Photoactivatable MOs can be introduced to achieve tissue-specific knockdowns in embryos [5]. And conjugation of dendrimeric octaguinidine to MOs (Vivo-MOs) results in permeability of MOs into cells [6]. Because of this membrane diffusible nature and lack of toxicity, use in human therapy is possible [7]. And Vivo-MOs can be employed to evaluate their use in treatment of Duchenne muscular dystrophy [8].

The present inventors utilized Vivo-MO technology to inhibit thrombocyte function in adult zebrafish for the first time by injecting thrombocyte-specific αIIb Vivo-MOs intravenously into adult zebrafish; thereby, established proof of principle and provided the basis to target two other novel candidate thrombocyte receptors, to knockdown thrombocyte function, and to evaluate the function of novel genes involved in, e.g., hemostatic pathways. The present inventors have shown that these novel receptors are present in human platelets and therefore this finding is applicable to human platelet function.

The present inventors recognize that currently available antisense oligonucleotide technologies include inhibition of protein synthesis by the siRNA, standard oligonucleotides (SOs), and modified oligonucleotides such as, phosphorothio oligonucleotide, locked oligonucleotides, and peptide nucleic acids. In all these approaches, delivery of the oligonucleotides into cells requires complexing these oligonucleotides with PEI or calcium phosphate precipitations. This methodology, however, cannot be used on whole organisms due to toxicity issues. The present inventors acknowledge that SOs are considered to be more toxic than phosphorothio nucleotides. In addition, when these antisense oligonucleotides are base-paired with the target mRNAs, the mRNAs are cleaved by RNaseH, and, therefore, appear to be more efficient than translational blocking or splice blocking induced by the morpholino oligonucleotides.

The present inventors recognize that if an SO is synthesized such that it is complementary to the target mRNA/pre-mRNA on the 5' side and complementary to a non-gene specific Vivo-MO (ngVMO) on the 3' side (FIG. 1), then this SO/ngVMO hybrid will enter the cell since the SO is 'piggy-backed' onto the ngVMO. Once inside the cell, in one embodiment, the SO portion binds to the target mRNA/pre-mRNA and leads to the cleavage of the target mRNA by the endogenous RNaseH mechanism. In other embodiments, the SO participates in splice and/or translation blocking using a mechanism similar to that of Vivo-MO targeting.

The present inventors demonstrate that in one non-limiting example or embodiment, a splice blocking SO specific for αIIb piggy-backed with ngVMO (αIIb-SO/ngVMO) can be used to inhibit thrombocyte function in adult zebrafish by intravenous injection. Furthermore, an SO specific for EGFP piggy-backed with ngVMO (EGFP-SO/ngVMO) can be used to inhibit EGFP in zebrafish thrombocytes. This targeting is not only efficient but also cost effective when compared to Vivo-MO targeting [9].

Zebrafish SO/ngVMO injections to generate knockdowns: A ngVMO 5'-CCTCTTACCTCAGTTACAATT-TATA-3' (SEQ ID NO: 1) was purchased from Gene-Tools LLC, Philomath Oreg. A SO was designed so that it can hybridize both to ngVMO (14 bp) and to αIIb pre-mRNA at the donor splice site of exon 20 (25 bp), 5'-GGAAGT-GACTAAACCCTCACCTCATTATAAATTGTAACTG-3' (SEQ ID NO: 2). A control SO that can hybridize to ngVMO and has a complementary sequence corresponding to the antisense sequence portion of the above SO, 5'-ATGAGGT-GAGGGTTTAGTCACTTCCTATAAATTGTAACTG-3' (SEQ ID NO: 3) was designed. Two other SOs were designed: one that targets EGFP mRNA and the other its control, 5'-TGTACATAACCTTCGGGCATGGCAC-TATAAATTGTAACTG-3' (SEQ ID NO: 4) and 5'-GTGC-CATGCCCGAAGGTTATGTACATATAAATTGTAACTG-3' (SEQ ID NO: 5), respectively. All SOs and their controls were purchased from Invitrogen, Carlsbad, Calif. 4.5 µl of 0.5 mM ngVMO was mixed with 4.5 µl of 0.5 mM SO and 1 µl 10× phosphate buffered saline, pH 7.4 (PBS). The mixture was heated at 90 degree C. and slowly cooled to room temperature so that the SO and ngVMO could hybridize. 5 µl of this hybridized SO/ngVMO was used to inject an adult zebrafish intravenously. αIIb-SO/ngVMO hybrid was injected into wild type zebrafish whereas EGFP-SO/ngVMO hybrid was injected into TG(fli1:EGFP)y1 zebrafish, which carries the transgene of the FLI1 gene promoter driving GFP and in which all thrombocytes are GFP positive.

Thrombocyte functional gill bleeding assay: Gill bleeding was induced by placing the fish in a petridish containing 50 ml of 50 µM NaOH. The fish were anesthetized in 50 ml of 2 mM tricaine (Sigma-Aldrich, St. Louis, Mo.) for 3 minutes prior to placing them in NaOH. The fish were photographed with a Nikon E995 Coolpix camera and the red pixels were counted by Adobe Photoshop software 7.0 and used to quantify bleeding.

RT-PCR: Zebrafish blood was centrifuged at 500 g and the white cell layer was used in the cell to cDNA kit (Agilent Technologies, LaJolla, Calif.) to amplify the αIIb mRNA. The present inventors designed forward 5'-AGTGCTG-CATGGACAAAGTG-3' (SEQ ID NO: 6) and reverse 5'-GGTTCTCCACCTGTTCCAGA-3' (SEQ ID NO: 7)

primers for exons 18 and 22, respectively; these were synthesized by Biosynthesis, Lewisville, Tex. These primers were used to amplify the 396 bp product. In the case of exon skipping, the predicted product is 149 base pair. These RT-PCR products were resolved on 1.5% agarose gels.

GFP fluorescence of thrombocytes: GFP fluorescence was detected on freshly prepared blood smears from EGFP-SO/ngVMO hybrid injected TG(fli1:EGFP)y1 transgenic zebrafish and was photographed for immunofluorescence using a Nikon Eclipse 80i microscope.

Statistical analysis: Statistical analysis was performed using Sigma Plot 10 with Sigma Stat integration software. Statistical significance was assessed by ANOVA and a p value <0.05 was considered significant.

Figure 2:
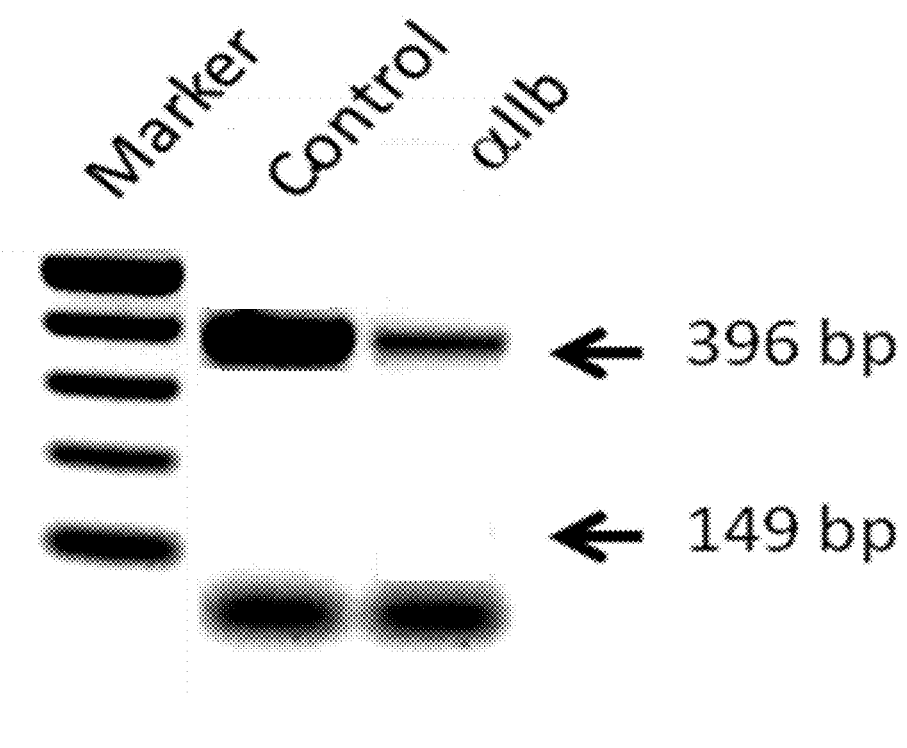
FIG. 2 shows αIIb-SO/ngVMO hybrid induced alternative splicing results in deletion of exon 20. Agarose gel showing the RT-PCR products from white cells including thrombocytes prepared from adult zebrafish injected with control SO hybrid (Control) and αIIb-SO/ngVMO hybrid (αIIb). Arrows show bands corresponding to the normal splice product (396 bp) and alternatively spliced product (149 bp). 2-log DNA Ladder (New England Biolabs, Ipswich, Mass.) used as DNA size markers (Marker) are in left lane.

To inhibit the synthesis of αIIb by knockdown method, the present inventors chose to splice out exon 20 of αIIb pre-mRNA; the present inventors have also targeted this exon in work using Vivo-MO specific for αIIb [9]. 5 µl αIIb-SO/ngVMO hybrid were injected intravenously into adult zebrafish and, after 24 hrs, RNA was isolated from white cell layer which contains thrombocytes. This RNA was analyzed for alternative splicing by using primers designed from exon 18 and 22 on RNA prepared from these thrombocytes. If normal splicing occurs, a 396 bp product is generated. If exon skipping occurs, a 149 bp of DNA is generated. A 149 bp band was obtained in the thrombocytes of zebrafish where αIIb-SO/ngVMO hybrid was injected compared to control SO hybrid (FIG. 2). Furthermore, the overall intensity of the 396 bp band was reduced and, in fact, in some experiments the band in this region was completely nonexistent.

Figure 3:
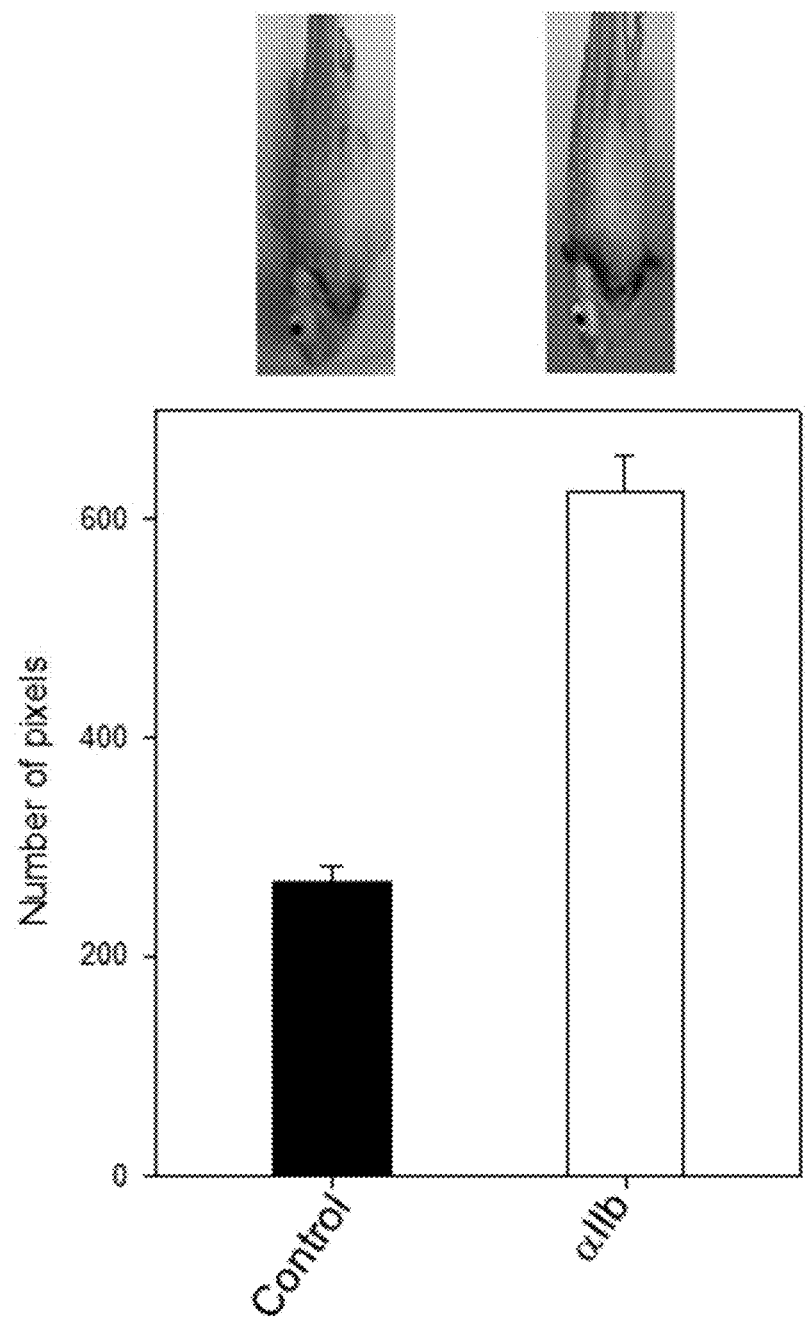
FIG. 3 shows gill-bleeding assay: Fish were photographed and the number of red pixels representing the bleeding were measured in control SO hybrid treated (Control) and αIIb-SO/ngVMO hybrid (αIIb) treated zebrafish (N=6). p value is <0.001 between the Control and αIIb.

Gill-bleeding assay was performed to show that the reduction in mRNA producing αIIb also result in greater bleeding. The fish treated with αIIb-SO/ngVMO hybrid exhibited more bleeding compared to the fish treated with control hybrid (FIG. 3).

EGFP synthesis was inhibited in thrombocytes that are GFP+ by injecting EGFP-SO/ngVMO hybrid intravenously into TG(fli1:EGFP)y1 transgenic zebrafish. Twenty-four hours after injection, a blood smear was prepared from these transgenic fish and GFP fluorescence in thrombocytes was observed: Almost 70-80% of thrombocytes lost GFP fluorescence (FIGS. 4a and 4b).

The present inventors demonstrate that, as a non-limiting example, direct injection of αIIb-SO/ngVMO hybrid intravenously into zebrafish inhibits αIIb and thus reduces thrombocyte aggregation. The RT-PCR results show that alternatively spliced αIIb mRNA is generated resulting in a 149 bp product (confirmed by sequence analysis) which provides evidence that the αIIb-SO/ngVMO hybrid is effectively penetrating thrombocytes. Interestingly, the effect of αIIb-SO/ngVMO hybrid on thrombocyte aggregation was also observed in 24 hrs. This result is similar to what the inventors observed with αIIb Vivo-MO [9]. However, the overall cumulative intensities of the 396 bp and 149 bp bands were reduced when compared to the 396 bp band in controls. This documents that, in addition to the alternative splicing due to splice blocking, the pre-mRNA is cleaved by RNaseH. Therefore, the EGFP study was conducted: SO were used that targets the EGFP mRNA sequence located approximately in the middle of translational initiation and terminator codons. Thus, the target is neither a translational blocker nor a splice blocker. Thus, reduction in EGFP in thrombocyte is due to the degradation of EGFP RNA by RNaseH mechanism. The results demonstrated 70-80% GFP− thrombocytes showing that the EGFP-SO/ngVMO hybrid method is very efficient and degrades EGFP RNA by RNaseH mechanism.

Because thrombocytes are readily accessible, the inhibition of αIIb in adult zebrafish provides therapeutic possibilities, provides the ability to inhibit the function of any thrombocyte specific gene and perform biochemical studies, and serves as a example of the predictability and feasibility to generally employ this methodology to other genes and other sequences. The present inventors recognize that, for example, thrombocyte surface receptors such as ADP receptors, thromboxane receptors, other GPCRs, and several signaling molecules, such as kinases, can be inhibited. Thus, this method has the advantage of inhibiting proteins for which small molecule inhibitors are not currently available. Furthermore, because of the ease of injections and thrombocyte assays, large-scale, high-throughput, genome-wide knockdowns can be designed to identify novel genes participating in thrombocyte development and function. In addition, the same principles can be used to understand other hematological disorders as well as disorders that are amenable for studies by simple injections of these hybrid SOs. Such genome-wide knockdowns are possible because SOs are significantly less expensive than MOs or Vivo-MOs. The present inventors recognize that some off-target knockdowns and toxicity are both inherent problems common to all antisense technologies. Nevertheless, after initial, large-scale screening, the toxic effects can be resolved by using less toxic phosphorothio oligonucleotides, which can also form hybrids similar to SOs, and off-target knockdown issues have to be confirmed by either genome TILLING or mutagenesis methods.

The present inventors have demonstrated that it is possible to inhibit thrombocyte specific function by exon skipping using αIIb-SO/ngVMO hybrids, and GFP expression can be eliminated from GFP+ thrombocytes in adult zebrafish by using EGFP-SO/ngVMO hybrids. This proof of principle of inhibition of protein expression in adult zebrafish by SO hybrids has tremendous applicability, not only to identify functions of novel genes in thrombocytes but also in other accessible blood cells as well as in highly vascular organs. Since it is possible to deliver SO hybrids to any hematopoietic cells, it is possible to use these reagents not only as an antithrombotic agent but also as an agent to correct other hematological disorders including AIDS by degrading HIV RNA. The efficiency of knockdowns can be increased by designing multiple SOs for the same target mRNA. Furthermore, by conducting random knockdowns of multiple protein functions, complex genetic disorders, such as diabetes, can be created in model organisms. In this way, the mechanisms of these and many other disorders come to light. In addition, RNAs and genes can be delivered easily into cells by complexing with the ngVMO, thus, this technology is applicable to gene therapy as well as RNA/protein therapies. Furthermore, efficient delivery of siRNA piggy-backed on ngVMO into the cells in whole organism should also be feasible. This allows for an additional, complementary approach to inhibit protein expression. Thus, the present technology has numerous applications.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] R. M. Hudziak, J. Summerton, D. D. Weller, and P. L. Iversen, Antiproliferative effects of steric blocking phosphorodiamidate morpholino antisense agents directed against c-myc. Antisense Nucleic Acid Drug Dev 10 (2000) 163-76.

[2] C. S. Cobbs, T. R. Whisenhunt, D. R. Wesemann, L. E. Harkins, E. G. Van Meir, and M. Samanta, Inactivation of wild-type p53 protein function by reactive oxygen and nitrogen species in malignant glioma cells. Cancer Res 63 (2003) 8670-3.

[3] A. Nasevicius, and S. C. Ekker, Effective targeted gene 'knockdown' in zebrafish. Nat Genet 26 (2000) 216-20.

[4] M. Gregory, R. Hanumanthaiah, and P. Jagadeeswaran, Genetic analysis of hemostasis and thrombosis using vascular occlusion. Blood Cells Mol Dis 29 (2002) 286-95.

[5] I. A. Shestopalov, S. Sinha, and J. K. Chen, Light-controlled gene silencing in zebrafish embryos. Nat Chem Biol 3 (2007) 650-1.

[6] P. A. Morcos, Y. Li, and S. Jiang, Vivo-Morpholinos: a non-peptide transporter delivers Morpholinos into a wide array of mouse tissues. Biotechniques 45 (2008) 613-4, 616, 618 passim.

[7] J. D. Moulton, and S. Jiang, Gene knockdowns in adult animals: PPMOs and vivo-morpholinos. Molecules 14 (2009) 1304-23.

[8] B. Wu, Y. Li, P. A. Morcos, T. J. Doran, P. Lu, and Q. L. Lu, Octa-guanidine morpholino restores dystrophin expression in cardiac and skeletal muscles and ameliorates pathology in dystrophic mdx mice. Mol Ther 17 (2009) 864-71.

[9] S. Kim, U. P. Radhakrishnan, S. K. Rajpurohit, V. Kulkarni, and P. Jagadeeswaran, Vivo-Morpholino knockdown of alphaIIb: A novel approach to inhibit thrombocyte function in adult zebrafish. Blood Cells Mol Dis 44 169-74.

| SEQUENCE LISTING | |
|---|---|
| CCTCTTACCTCAGTTACAATTTATA | SEQ ID NO: 1 |
| GGAAGTGACTAAACCCTCACCTCATTATAAATTGTAACTG | SEQ ID NO: 2 |
| ATGAGGTGAGGGTTTAGTCACTTCCTATAAATTGTAACTG | SEQ ID NO: 3 |
| TGTACATAACCTTCGGGCATGGCACTATAAATTGTAACTG | SEQ ID NO: 4 |
| GTGCCATGCCCGAAGGTTATGTACATATAAATTGTAACTG | SEQ ID NO: 5 |
| AGTGCTGCATGGACAAAGTG | SEQ ID NO: 6 |
| GGTTCTCCACCTGTTCCAGA | SEQ ID NO: 7 |

What is claimed is:

1. A nucleic acid hybrid molecule capable of entering cells comprising:
   at least one vivo-morpholino oligonucleotide (vivo-MO) comprising a guanidine-rich head at the 5' end; and
   at least one oligonucleotide comprising a gene-specific sequence and a oligonucleotide pairing sequence, wherein the oligonucleotide is bound to the vivo-morpholino oligonucleotide through base pairing to form a hybrid; and
   wherein the vivo-morpholino oligonucleotide pairing sequence is complementary to the oligonucleotide pairing sequence.

2. The nucleic acid hybrid molecule of claim 1, wherein the oligonucleotide comprises a RNA.

3. The nucleic acid hybrid molecule of claim 1, wherein the oligonucleotide comprises a siRNA or a RNAi.

4. A method of introducing a oligonucleotide into a cell comprising:
   obtaining a oligonucleotide comprising a gene-specific sequence and a oligonucleotide pairing sequence;
   obtaining a vivo-morpholino oligonucleotide (vivo-MO) comprising a guanidine-rich head conjugated to the 5' end and a vivo-morpholino oligonucleotide pairing sequence that is complementary to the oligonucleotide pairing sequence;
   binding the oligonucleotide to the vivo-morpholino oligonucleotide, wherein a nucleic acid hybrid molecule is formed; and
   contacting a cell with the nucleic acid hybrid molecule.

5. The method of claim 4, wherein the cell has been previously isolated.

6. The method of claim 4, wherein contacting the cell with the nucleic acid hybrid molecule is selected from the group consisting of administering the nucleic acid hybrid molecule to a vertebrate orally, intravenously, intramuscularly, intraperitoneally, subcutaneously, by intranasal instillation, by application to mucous membranes, and by instillation into hollow organ walls or newly vascularized blood vessels.

7. The method of claim 4, wherein contacting the cell with the nucleic acid hybrid molecule comprises treating a patient afflicted with a disease selected from the group consisting of diabetes, cancer, thalassemia, sickle cell disease, hemophilia, viral hepatitis, AIDS, genetic disease, and infectious disease.

8. The method of claim 4, further comprising determining a gene expression of a gene complementary to the gene-specific sequence.

9. The method of claim 4, wherein the oligonucleotide is selected from the group consisting of a DNA oligonucleotide, a RNA, a RNAi, a siRNA, phosphorodithio oligonucleotide, a phosphorothio oligonucleotide, a locked oligonucleotide, and a peptide nucleic acid.

10. The method of claim 4, wherein the oligonucleotide comprises a gene.

11. The method of claim 4, wherein the guanidine-rich head comprises a dendrimeric octaguinidine.

12. A method to treat a patient suspected of having a disease comprising:
    obtaining a nucleic acid hybrid molecule capable of entering cells comprising at least one oligonucleotide comprising a gene-specific sequence and a oligonucleotide pairing sequence, at least one vivo-morpholino oligonucleotide (vivo-MO) comprising a guanidine-rich head conjugated to the 5' end, wherein the vivo-morpholino oligonucleotide pairing sequence is complementary to the oligonucleotide pairing sequence, and wherein the oligonucleotide is bound to the vivo-morpholino oligonucleotide through base pairing, forming a hybrid; and
    contacting the patient with the nucleic acid hybrid molecule.

13. The method of claim 12, further comprising:
    obtaining a sample from the patient; and
    determining gene expression of a gene that is homologous, antisense, or complementary to the gene-specific sequence.

14. The method of claim 12, wherein the disease is selected from the group consisting of diseases treatable by reducing a translation of a gene, wherein the gene is a c-myc gene and the disease is Burkitt's lymphoma or the gene is a ras oncogene and the disease is adenocarcinomas, a thyroid tumor, or a pancreatic tumor.

15. The method of claim 12, wherein contacting the patient with the nucleic acid hybrid molecule is selected from the group consisting of administering the nucleic acid hybrid molecule orally, intravenously, intramuscularly, intraperitoneally, subcutaneously, by intranasal instillation, by application to mucous membranes, and by instillation into hollow organ walls or newly vascularized blood vessels.

16. The method of claim 12, wherein the oligonucleotide is selected from the group consisting of a DNA oligonucleotide, a RNA, a RNAi, a siRNA, a phosphorodithio oligonucleotide, a phosphorothio oligonucleotide, a locked oligonucleotide, and a peptide nucleic acid.

17. A method of performing a clinical trial to evaluate a candidate drug believed to be useful in treating a disease by affecting the expression of a gene complementary, antisense, or homologous to a gene-specific sequence, the method comprising:
    (a) obtaining the candidate drug comprising a nucleic acid hybrid molecule capable of entering cells comprising at least one oligonucleotide comprising the gene-specific sequence and a oligonucleotide pairing sequence; at least one vivo-morpholino oligonucleotide (vivo-MO) comprising a guanidine-rich head conjugated to the 5' end; wherein the vivo-morpholino oligonucleotide pairing sequence is complementary to the oligonucleotide pairing sequence; and wherein the oligonucleotide is bound to the vivo-morpholino oligonucleotide through base pairing, forming a hybrid;
    (b) administering the candidate drug to a first subset of patients, and
    a placebo to a second subset of patients;
    a comparable drug to a second subset of patients; or a drug combination of the candidate drug and another active agent to a second subset of patients; and (c) monitoring the progression of the disease in the first subset of patients as compared to the second subset of patients, wherein a relative and statistically significant improvement of the disease in the first subset of patients indicates that the candidate drug is useful in treating the disease.

18. A method to identify a nucleic acid hybrid molecule effective in reducing an expression of a gene comprising:

obtaining a first and at least a second nucleic acid hybrid molecule, each nucleic acid hybrid molecule comprising at least one oligonucleotide comprising a sequence specific for the gene and a oligonucleotide pairing sequence; each nucleic acid hybrid molecule further comprising at least one vivo-morpholino oligonucleotide (vivo-MO) comprising a guanidine-rich head conjugated to the 5' end, wherein the vivo-morpholino oligonucleotide pairing sequence is complementary to the oligonucleotide pairing sequence, and wherein the oligonucleotide is bound to the vivo-morpholino oligonucleotide through base pairing, forming a hybrid, contacting the first and at least the second nucleic acid hybrid molecules with at least one cell each;

determining the expression of the gene in the cells contacted with the first and at least the second nucleic acid hybrid molecules; and identifying the nucleic acid hybrid molecules effective in reducing the expression of the gene.

19. The method of claim 18 further comprising:
determining the expression of a control gene; and
identifying the nucleic acid hybrid molecule that does not affect the expression of the control gene.

20. A method to reduce an expression of a gene comprising:

obtaining a oligonucleotide comprising a gene-specific sequence and a oligonucleotide pairing sequence;

obtaining a vivo-morpholino oligonucleotide (vivo-MO) comprising a guanidine-rich head conjugated to the 5' end and a vivo-morpholino oligonucleotide pairing sequence that is complementary to the oligonucleotide pairing sequence;

binding the oligonucleotide to the vivo-morpholino oligonucleotide, wherein a nucleic acid hybrid molecule is formed; and contacting at least one cell with the nucleic acid hybrid molecule, whereby the hybrid molecule enters the cell and whereby the nucleic acid hybrid molecule reduces the expression of the gene.

21. The method of claim 20, wherein contacting the cell with the nucleic acid hybrid molecule is selected from the group consisting of administering the nucleic acid hybrid molecule orally, intravenously, intramuscularly, intraperitoneally, subcutaneously, by intranasal instillation, by application to mucous membranes, and by instillation into hollow organ walls or newly vascularized blood vessels.

22. The method of claim 20, wherein contacting the cell with the nucleic acid hybrid molecule comprises treating a patient afflicted with a disease selected from the group consisting of diabetes, cancer, genetic disease, and infectious disease.

23. The method of claim 20, wherein the oligonucleotide is selected from the group consisting of a DNA oligonucleotide, a RNA, a RNAi a siRNA, a phosphorodithio oligonucleotide, a phosphorothio oligonucleotide, a locked oligonucleotide, and a peptide nucleic acid.

24. The method of claim 20, wherein the guanidine-rich head comprises a dendrimeric octaguinidine.

* * * * *

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: synthetic primer

<400> SEQUENCE: 1
cctcttacct cagttacaat ttata                                             25

<210> SEQ ID NO 2
<211> LENGTH: 40
<212> TYPE: DNA
<213> ORGANISM: Artificial Sequence
<220> FEATURE:
<223> OTHER INFORMATION: synthetic primer

<400> SEQUENCE: 2
ggaagtgact aaaccctcac ctcattataa attgtaactg                             40

<210> SEQ ID NO 3
<211> LENGTH: 40
<212> TYPE: DNA
<213> ORGANISM: Artificial Sequence
<220> FEATURE:
<223> OTHER INFORMATION: synthetic primer

<400> SEQUENCE: 3
atgaggtgag ggtttagtca cttcctataa attgtaactg                             40

<210> SEQ ID NO 4
<211> LENGTH: 40
<212> TYPE: DNA
<213> ORGANISM: Artificial Sequence
<220> FEATURE:
<223> OTHER INFORMATION: synthetic primer

<400> SEQUENCE: 4
tgtacataac cttcgggcat ggcactataa attgtaactg                             40

<210> SEQ ID NO 5
<211> LENGTH: 40
<212> TYPE: DNA
<213> ORGANISM: Artificial Sequence
<220> FEATURE:
<223> OTHER INFORMATION: synthetic primer

<400> SEQUENCE: 5
gtgccatgcc cgaaggttat gtacatataa attgtaactg                             40

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
agtgctgcat ggacaaagtg                                                   20

<210> SEQ ID NO 7
<211> LENGTH: 20
<212> TYPE: DNA
<213> ORGANISM: Artificial Sequence
```

```
<220> FEATURE:
<223> OTHER INFORMATION: synthetic primer

<400> SEQUENCE: 7
ggttctccac ctgttccaga                                                    20
```